United States Patent [19]

Sato et al.

[11] Patent Number: 4,978,389

[45] Date of Patent: Dec. 18, 1990

[54] SURFACE TREATING AGENT AND THE PROCESS THEREFOR

[75] Inventors: Masayuchi Sato, Tokyo; Atsushi Mori, Chiba; Mamoru Aizawa, Ichihara, all of Japan

[73] Assignee: Nippon Soda Co. Ltd., Japan

[21] Appl. No.: 317,052

[22] Filed: Feb. 27, 1989

Related U.S. Application Data

[63] Continuation of Ser. No. 64,068, Jun. 18, 1987, abandoned.

[30] Foreign Application Priority Data

Jun. 18, 1986 [JP] Japan ................................ 61-140235

[51] Int. Cl.$^5$ ...................... C09D 173/00; C07F 7/28
[52] U.S. Cl. .................................. 106/14.41; 556/55; 556/56; 528/395; 528/401; 526/241
[58] Field of Search .................... 556/55, 56; 528/395, 528/401; 526/241; 106/14.41

[56] References Cited

U.S. PATENT DOCUMENTS

| | | | |
|---|---|---|---|
| 2,643,262 | 6/1953 | Bostwick | 556/56 |
| 2,809,990 | 10/1957 | Brown | 556/55 |
| 2,888,367 | 5/1959 | Greyson | 556/56 |
| 3,250,808 | 5/1966 | Moore et al. | 252/33.6 |
| 4,056,356 | 11/1977 | Gilkey et al. | 528/275 |
| 4,524,201 | 6/1985 | Barnabeo et al. | 528/395 |

*Primary Examiner*—Gary P. Straub
*Assistant Examiner*—Stuart L. Hendrickson
*Attorney, Agent, or Firm*—Bryan, Cave, McPheeters & McRoberts

[57] ABSTRACT

Surface treating agents comprising of an organic titanium compound containing at least one fluoropolyether radical linked by carboxy groups to the titanium and at least one hydrolyzable group, such compounds being obtained by reacting a fluoropolyether having one or more carboxylic groups with a titanium compound having at least one group able to react with carboxylic group and at least one residual hydrolyzable group per titanium atom. The surface treating agents have not only superior surface activity and anti-corrosion properties for the metal surface but are also chemically stable.

10 Claims, 2 Drawing Sheets

SURFACE TREATING AGENT AND THE PROCESS THEREFOR

This is a continuation of U.S. application Ser. No. 07/064,068, filed June 18, 1987, now abandoned.

FIELD OF TECHNOLOGY

This invention relates to fluoropolyether surface treating agents, more particularly to new surface treating agents obtained by reaction of a fluoropolyether having carboxylic acid groups with a titanium compound having at least one group able to react with the carboxylic group and at least one residual hydrolyzable group.

The surface treating agents of the present invention are excellent as wetting agents and have anticorrosion properties for the surface of metals, resistance to chemicals and to fouling. For these reasons they can be used in the fields in which perfluoropolyether oils have traditionally been used, such as vacuum pump oil, lubrication oil, sealing oil, mould releasing agent and damper liquid, either alone or as an additive for perfluoropolyether oils to improve their characteristics.

BACKGROUND TECHNOLOGY

There are known chemically stable and inert oil compounds containing fluorine, for instance, polychlorotrifluoroethylene, perfluoropolyethers and perfluoroalkanes, for the applications indicated above. However, compounds containing chlorine can dechlorinate and corrode metal materials in the presence of water. See, for example, "Advanced Technology of Halogen Chemicals", pages 214 to 215, C.M.C. Co. (1984). Fluoridated oils, in particular perfluoropolyethers not containing hydrogen and/or chlorine atoms, have excellent stability for use in many applications.

In general however the perfluoropolyethers do not have sufficiently good anticorrosion properties for many applications.

Perfluoropolyether oils do not have sufficient surface activity for many purposes; see for example Shinku, vol. 28, No. 6, pp. 483–485 (1985) and Chemistry and Industry of the Magnetic Body, pages 52 to 55, Techmart Co., (1978). Even by adding organic acids as surface active agents to perfluoropolyethers, for instance, penta-(perfluoropropylene oxide)-perfluoropropanoic acid, desorption of the surface treating agent takes place at 65° C., so that it is extremely difficult to improve the surface activity at temperatures higher than 65° C. (Chemistry and Industry of the Magnetic Body, p. 39, cited above).

In addition to this, said perfluoropolyethers, though having excellent chemical stability, when containing the additives mentioned above have the disadvantage to corroding the metal surface. This must be completely avoided when the perfluoropolyethers are employed for magnetic media in which the magnetic substance itself is very fine metal powder.

DETAILED DESCRIPTION OF THE INVENTION

The present invention provides new surface treating agents prepared by reacting a fluoropolyether having carboxylic acid groups with a titanium compound having at least one group able to react with the carboxylic group and at least one hydrolyzable group per titanium atom. The new agents have excellent surface adhesion and impart excellent anticorrosion properties to the surface of metal. These new compounds can be used as such or as additives to perfluoropolyether oils.

Applicants have found that the product of reaction of a fluoropolyether having carboxylic groups with a titanium compound, in particular alkoxide or its derivatives, imparts a considerable change in the metal surface activity and overcome the disadvantages of the products known in the art.

The new fluoropolyether surface treating agent consists of an organic titanium compound having per Ti atom at least one radical (A) of fluoropolyether linked by a carboxy group to the titanium and one or more hydrolyzable groups (B). In particular, the hydrolyzable group, is an alkoxy group preferably a radical of monovalent alcohol of 1 to 8 carbon atoms having a straight or branched chain which may be substituted, a radical corresponding to mono-valency of di-valent alcohol of 2 to 3 carbon atoms, a radical of β-di-ketones, such as preferably acetylacetone, and a radical of β-keto-ester. The invention also concerns the process for preparing said surface treating agents.

The surface treating agent of the invention is an organic titanium compound which in monomer form is expressed by the following general formula:

where A stands for said fluoropolyether carboxy radical and B stands for said hydrolizable group and a is an integer from 1 to 3 and preferably from 1 to 2; in polymer form contains in the molecule the linkage Ti—O—Ti corresponding to the general formula being in which b is an integer from 0 to 4 and the valences of the Ti are saturated by A and B and having per Ti atom at least one radical A and one radical B as defined above; the hydrolyzable radical B being such not to generate Hhal by hydrolysis, hal being Cl or Br.

The invention also concerns mixtures of the compounds in monomer and in polymer form.

The substituent A is preferably a carboxy radical derived from fluoropolyethers having one or more of the following repeating units represented by the general formula $(C_nF_{2n}O)$ wherein n ranges from 1 to 3 in the case of the polyfluoroxyalkylene units.

The oxypolyfluoroalkylene chain can comprise, in particular, recurrent units of the following types:

(I) $(CF_2CF_2O)$, $(CF_2O)$, said units being randomly distributed along the polyfluoropolyether chain;

(II)

with X=F or CF$_3$, said units being randomly distributed along the polyfluoropolyether chain;

(III)

with X=F or CF$_3$, with said units being randomly distributed along the polyfluoropolyether chain;

(IV)

(V) (CH$_2$CF$_2$CF$_2$O);
(VI) (CF$_2$CF$_2$CF$_2$O);
(VII) —(—CF$_2$—CF$_2$—CH$_2$O)$_0$—R'$_f$—O—(CH$_2$CF$_2$—CF$_2$—O)$_q$—
wherein R'$_f$ is a fluoroalkylene group, p and q are integers from 0 to 200; and p+q is at least 2;
(VIII)

wherein R"$_f$ is a fluoroalkylene group, n' is either 0 or 1, a' and b' are integers, and a'+b' is at least 2;
(IX) (CF$_2$CF$_2$O),
(X)

wherein R$_f$ equal or different is F or a perfluoroalkyl group;
(XI) (CF$_2$OCF$_2$CF$_2$O).

The polyfluoropolyether starting materials belonging to classes II, III, VI, IX, and X can be functionalized, if necessary, to both of their ends, by applying, e.g., the scission process as disclosed in Italian patent application No. 22,920 A/85, hereby incorporated by reference in its entirety, which yields acidic end groups —COF, easily convertible to a carboxylic group by using the teaching of the hereunder described patents.

See, in particular, U.S. Pat. Nos. 3,810,874 and 3,847,978, and Italian Patent No. 903,446, all of which are hereby incorporated by reference.

As the fluoropolyether starting materials can be used products, which are widely known in the art and disclosed, in particular, in the following patent or patent applications: U.S. Pat. Nos. 3,242,218; 3,665,041; 3,715,378; EPO No. 151,877, now U.S. Pat. No. 4,647,413; U.S. Pat. No. 4,523,039; WO No. 87/00538, now U.S. Pat. No. 4,675,452; all of which are hereby incorporated by reference in their entirety.

The carboxylic group can be linked to the fluoroalkylenoxy unit through the bivalent radical —C$_{p"}$F$_{2p"}$— wherein p" is 1 or 2 and optionally through a further bridge radical —(Z)$_{p'}$— in which p' is 0 or 1 for instance —(CH$_2$—)$_t$ (t=1-4), —CH$_2$OCH$_2$— —(CH$_2$CH$_2$O)$_t$CH$_2$—, —CONHCH$_2$CH$_2$—.

As already said the fluoropolyethers used as starting material in the invention can have one carboxylic group in the case of monofunctional fluoropolyether, the other terminal group being a perfluoroalkoxy group having 1-3 C atoms. In the case of bifunctional compounds instead of the polyfluoroalkoxy group there is a group

—OC$_{p"}$F$_{2p"}$—(Z)$_{p'}$—COOH.

The average molecular weight of the carboxyfluoropolyether radical A is comprised in general between 400 and 8000 and preferably between 700 and 4000, measured as number average molecular weight.

The radical B is a hydrolyzable group in the sense that by reaction with H$_2$O, the Ti-B bond forms a —Ti—OH and a BH compound.

In particular B is an RO— group in which R is alkyl optionally substituted for example by —OH, —NH$_2$, alkenyl, or an enolate form of β-di-keto-compounds or of β-ketoesters.

Group (B) in particular is selected from the group consisting of a radical of mono-valent alcohol shown by the group RO— (wherein R means alkyl group or alkenyl group of 1 to 8 carbon atoms having a straight or branched chain which may be substituted) for instance, CH$_3$O—, C$_2$H$_5$O—, i=C$_3$H$_7$O—, n=C$_4$H$_9$O—, C$_8$H$_{17}$O—, NH$_2$CH$_2$CH$_2$O—, CH$_2$=CH—CH$_2$O—; or a radical corresponding to a di-valent alcohol shown by the groups,

(wherein R' and R" mean either the same or different —CH$_2$—, for instance:

or acetylacetone or ketoester radical (wherein Y means either a methyl group or an alkoxy group of 1 to 4 carbon atoms) for instance methyl acetoacetate, ethyl acetoacetate, propyl acetoacetate and butyl acetoacetate. Other hydrolyzable groups are of the type —NR$_1$R$_2$ wherein R$_1$ and R$_2$ have the same meaning of R indicated above. These hydrolyzable groups need not to be one alone but may be more than one.

Organic titanium compounds having substituents as described above can be prepared by reacting a carboxylic fluoropolyether indicated above with a titanium compound B₄Ti which has said hydrolyzable groups.

The reaction is carried out by adding under stirring an equivalent of 1 to 3 of the carboxylic group of fluoropolyether (FPCA), preferably an equivalent of 1 to 2 per mol of Ti atom of the starting titanium compound, usually in an organic solvent for a period of 20 minutes to 4 hours at temperatures ranging from 10° to 80° C. In this reaction according to the selection of reaction conditions such as the type of the starting material and the solvent, the monomer alone of the organic titanium compound, or a mixture of the monomer with polymer, as indicated above, is synthetically prepared. Particularly in the system where an excess of FPCA is present, the esterification reaction with alcohol eliminated from FPCA and the starting titanium compound takes place as side reaction and water is formed as by-product, permitting the condensation polymerization by hydrolysis of the titanium compound which has not yet reacted, and an organic titanium compound polymer having the linkage —Ti—O—Ti— in the molecule is apt to be formed and corresponds to the general formula:

wherein b ranges from 0 to 4;

The starting titanium derivatives can be easily prepared by contacting a titanium alkoxide having 4 alkoxyl groups with at least one compound selected from divalent alcohol, acetylacetone, and β-keto-ester either in the presence or in the absence of an organic solvent. The organic titanium compound having a hydrolyzable group other than the alkoxy group may be obtained by reacting FPCA with titanium alkoxide, followed by reaction of at least one compound selected from the group consisting of di-valent alcohol, acetylacetone, and keto-ester in an amount corresponding to the alkoxy groups to be substituted. Preferably it is substituted with only one alkoxide group. Further, the organic titanium compound polymer having in the molecule the Ti—O—Ti linkage and FPCA radical and alkoxy group, as substituent groups, can be selectively obtained by reacting with FPCA a polytitanoxane having in the molecule the Ti—O—Ti linkage and alkoxy group as the substituent group. The polytitanoxane is prepared by submitting titanium alkoxide to the preliminary polycondensation. Still further, the intended organic titanium compound polymer having a hydrolyzable group other than the alkoxy group can be selectively synthesized by reacting said polymer with at least one compound selected from the group consisting of di-valent alcohol, acetylacetone, and β-keto-ester. The surface treating agent of the invention can be applied to the surface of the substrate by coating the said organic titanium compound alone or in an organic solvent and then drying. Iron, steel, copper and like metals can be the substrate. Also, magnetic powder, ceramic powder, and ceramic moulded articles can be treated likewise.

Furthermore, the surface treating agents of this invention can be admixed with perfluoropolyether oils to reduce wear and prevent the corrosion of the surface of the metal or ceramic. The amount of the surface treating agent of this invention to be added to perfluoropolyether oil is generally 0.1 to 2.0 parts by weight of the organic titanium compound to 100 parts by weight of oil when the oil is vacuum pump oil and lubricating oil, and generally 1 to 10 parts by weight of the organic titanium compound to 100 parts by weight of oil when used as magnetic fluid, said amounts being enough to achieve the object of the invention.

The surface treating agent of this invention is characterized in that it is a new organic titanium compound having, as already mentioned, both an unhydrolyzable FPCA radical and a hydrolyzable group.

When this surface treating agent is applied onto the surface of a substrate, the adsorbed water or —OH group present on the surface of the substrate reacts with the hydrolyzable group of said organic titanium compound and hydrolyzes said organic titanium compound to form M—O—Ti (M means the atom present on the surface of the substrate such as metal atom), causing at the same time the formation of the Ti—O—Ti linkages. All these linkages, it has been found unexpectedly, prevent the corrosion of the surface of the substrate while the FPCA radical layer is water and oil repellent. Accordingly, the application of the surface treating agent of the present invention causes the formation on the surface of the substrate a coated film having excellent repellency to water and oil and resistance to corrosion.

When the surface treating agent of this invention is used in admixture with polyperfluoroalkylenether oil, it has been found that the surface activity of the latter improves to a considerable degree lubrication and anti-corrosion properties.

In order to obtain these results the organic titanium compound must have at least one hydrolyzable group and at least one FPCA radicals for each Ti atom.

To further illustrate the invention and its advantages, the following examples are provided.

BEST MODE FOR CARRYING OUT THE INVENTION (1) Synthetic Preparation of Organic Titanium Compound (a) Sample (T-1)

A four-necked flask of 300 cc in capacity, equipped with a stirrer, reflux condenser, thermometer, and dropping device, was charged with 28.4 g (0.1 mol) of tetraisopropoxytitanium and 71.8 g of polyperfluoroalkylene ether carboxylic acid [F(C₃F₆O)₃.₃CF(CF₃)COOH] were added dropwise with stirring over 4 hours with exterior cooling so that the reaction solution might not be heated beyond 40° C.

After the dropwise addition came to an end, the reaction product was maintained under stirring for 2 hours at said temperature.

The reaction solution so obtained was charged into a rotary evaporator and removed of the volatile matter for 4 hours at a bath temperature of 45° C. and 20 Torr. As a result, 5.2 g of isopropanol were obtained as distillate. The residue so obtained was a colorless transparent viscous liquid (T-1).

The obtained (T-1) has no free carboxylic acid and is slightly soluble in carbon tetrachloride.

Figure 1A:
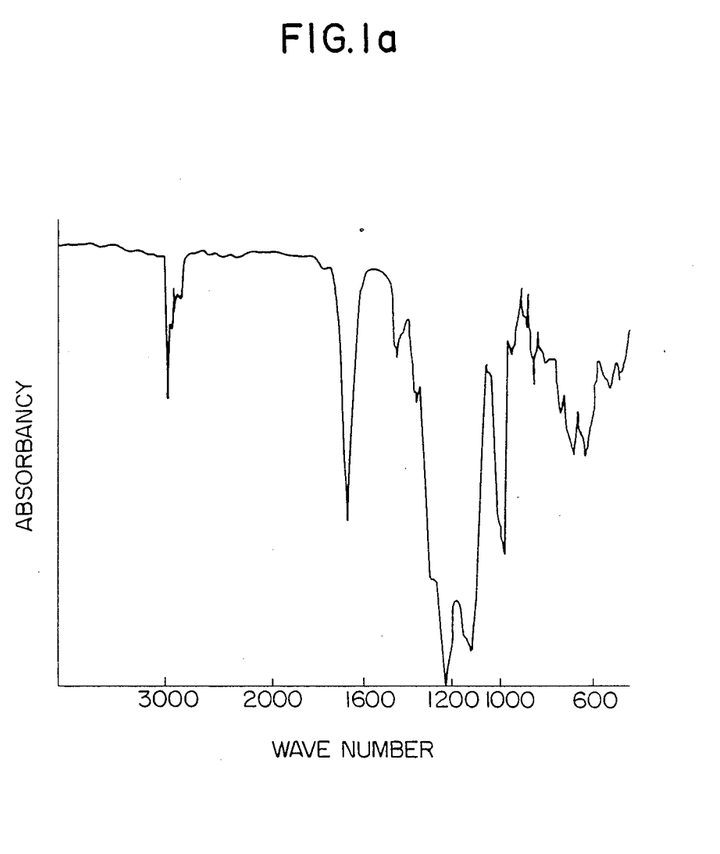
FIG. 1(a) shows the infrared absorption spectrum of a surface treating agent of this invention and FIGS. 1(b) and 1(c) are infrared absorption spectra for its starting compounds, tetraisopropoxytitanium and polyperfluoroalkylene ether carboxylic acid, respectively.
Figure 1B:
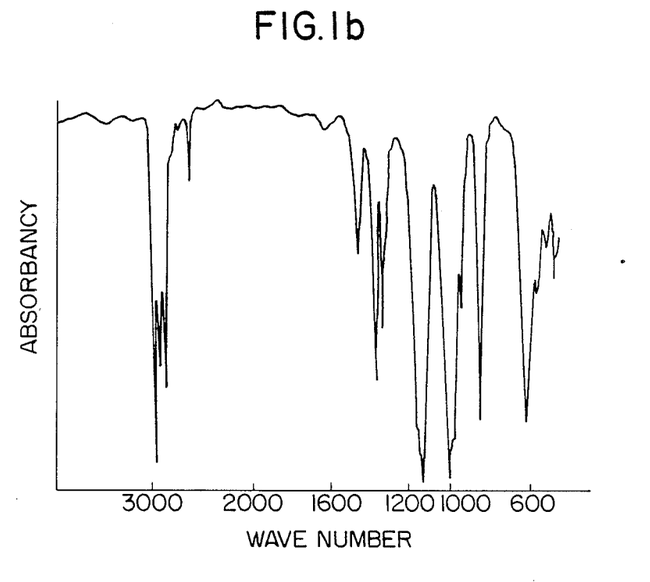
Figure 1C:
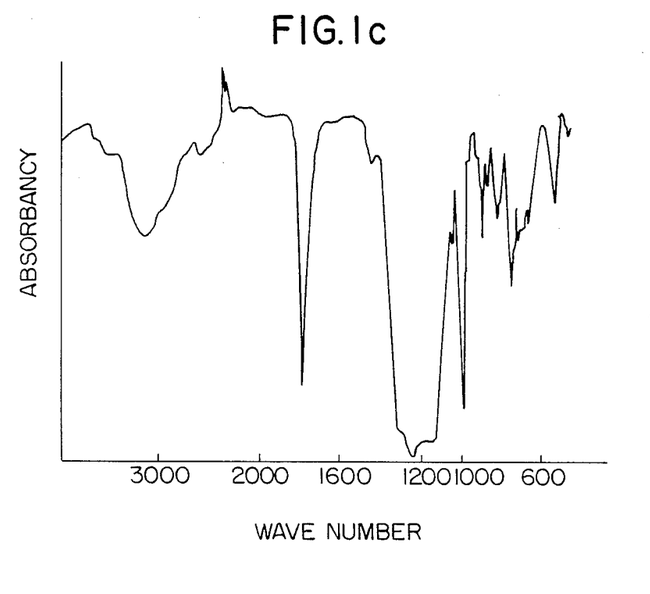

The infra-red absorption spectrum of (T-1) is shown in FIG. 1(a), that of the starting tetraisopropoxytitanium in FIG. 1(b), and that of polyperfluoroalkylene ether carboxylic acid in FIG. 1(c).

As shown in FIG. 1(a), (T-1) has the absorption due to —COOTi at 1670 cm$^{-1}$ and the absorption of 1780 cm$^{-1}$, based on —COOH found in the starting polyperfluoroalkylene ether carboxylic acid, has disappeared.

From the aforesaid infra-red spectra and from the amount of the isopropanol distillate (about 0.1 mol), (T-1) was presumed to be tris(2-propanolate)titanium-polyperfluoroalkylene ether carboxylate.

(b) Sample (T-2)

10 g of the (T-1) synthetically prepared as in the foregoing (a) were introduced into the same reaction apparatus, to which 0.6 g of ethylene glycol were added, and the mixture was maintained under stirring. A white opaque highly viscous liquid was obtained. The liquid so obtained was charged into a rotary evaporator to remove the volatile matter for 4 hours at a bath temperature of 50° C. and 20 Torr. 1 g of distillate resulted and a semi-transparent viscous liquid (T-2) was obtained at over 40° C.

The distillate was found to be isopropanol as a result of the analysis by gas-chromatography.

(T-2) was slightly soluble in carbon tetrachloride.

(T-2) was presumed to be (T-1) in which one 2-propanolate group was substituted by one ethylene glycol radical.

(c) Sample (T-3).

A 500 cc four-necked flask, provided with a stirrer, reflux condenser, thermometer, and dropping device, was charged with 142 g (0.5 mol) of tetraisopropoxytitanium, 50 g (0.5 mol) of acetylacetone being added dropwise under stirring in the course of 2 hours and the system was cooled so that the reaction temperature did not exceed 40° C.

10 g of the resulting yellow and transparent reaction solution were put into a 200 cc four-necked flask provided with a stirrer, reflux condenser, thermometer, and dropping device, and 36 g of the polyperfluoroalkylene ether carboxylic acid [F(C$_3$F$_6$O)$_{3.3}$CF(CF$_3$)COOH] were added dropwise under stirring over 3 hours and the mixture was cooled so that the temperature did not exceed 40° C. A yellow slightly turbid viscous liquid (T-3) was obtained.

(T-3) was slightly soluble in carbon tetrachloride.

(T-3) was presumed to be T-1 in which two 2-propanolate groups were substituted by one acetone radical and one polyperfluoroalkylene ether carboxylic acid radical.

(d) Comparative Sample (CT-1).

A 400 cc four-necked flask with a stirrer, reflux condenser, thermometer, and dropper was charged with 9 g of perfluorocaprylic acid (n—C$_7$F$_{15}$COOH) and then dissolved in 200 g of n-hexane under stirring. Then 3.6 g of tetraisopropoxytitanium were slowly added dropwise under stirring by means of a dropper, the reaction temperature being maintained between 20° and 30° C. The mixture was maintained under stirring for another three hours to obtain a colorless transparent liquid (CT-1).

The so obtained (CT-1) had 5.3 per cent of non-volatile matter.

(2) Test on Repellency to Oil

Deck glasses for the microscope were thoroughly washed, dipped in n-hexane, taken out and dried.

One deck glass treated in the manner mentioned above was dipped into a solution of 1% organic titanium compound in carbon tetrachloride of T-1 and another deck glass into a solution prepared in the same way of (CT-1). Then the glasses were drawn up, rinsed immediately with fresh n-hexane, shaken off to remove the n-hexane, and dried for 30 minutes at 60° C.

Onto the deck glasses treated in the manner described above and also onto the untreated clean deck glass one drop of polyperfluoroalkylene ether oil (product of Montedison S.p.A., Fomblin ® Y) and one drop of a liquid paraffin were put to determine the contact angle.

The results of determination are shown in Table 1.

TABLE 1

|  | Example | Comparative Example | |
|---|---|---|---|
| Number | 2-1 | 2-1 | 2-2 |
| Surface treating agent | T-1 | CT-1 | Not treated |
| Fomblin ®Y | 23° | 58° | 25° |
| Liquid paraffin | 75° | 80° | 18° |

As shown in Table 1 the surface of the glass treated with the surface treating agent of this invention (T-1) exhibits repellency to oil against liquid paraffin and a comparable degree of affinity with polyperfluoroalkylene ether oil to the surface of clean untreated glass. In contrast, the surface of glass treated with the Comparative Sample (CT-1) shows repellency to oil against both liquid paraffin and polyperfluoroalkylene ether oil.

(3) Test on Corrosion

Steel plates 0.5×50×150 mm in size (JIS-G-3141), which were preliminarily degreased with trichloroethylene, washed, dipped into n-hexane and dried, were dipped respectively in CCl$_4$ solutions of 1% by weight of the samples (T-1), (T-2), (T-3) and in the solution of (CT-1) for five minutes, drawn up, and washed with fresh carbon trachloride. Thereafter the plates were maintained at a temperature of 60° C. for a period of 30 minutes.

Also, for comparison, a steel plate was treated with a commercially available solution of titanium coupling agent (CT-2) composed of isopropoxytitanium triisostearate as the main component.

The steel plates and untreated plate were coated with polyperfluoroalkylene ether oil (product of Montedison S.p.A., Fomblin ®Z) and hung in a dessiccator charged with 100 g of carbon tetrachloride in which 1 g of chlorine was dissolved and with 100 g of distilled water. This was left undisturbed at room temperature to observe the development of rust on the steel plates.

Results are shown in Table 2.

TABLE 2

| | Test Number | Surface Treating Agent | After One Week | After Two Weeks |
|---|---|---|---|---|
| Examples | 3-1 | T-1 | No rust developed | No rust developed |
| | 3-2 | T-2 | No rust developed | Rust developed in a spot-like way |
| | 3-3 | T-3 | No rust developed | Rust developed in a spot-like way |
| Comparative | 3-1 | CT-1 | Spot-like rust | Spot-like rust |

TABLE 2-continued

| Example | Test Number | Surface Treating Agent | After One Week | After Two Weeks |
|---|---|---|---|---|
| | | | developed | spread to cover 1/10 of the total area |
| | 3-2 | CT-2 | Rust developed in ¼ of the total area | Rust developed in ½ of the total area |
| | 3-3 | | Rust developed in ½ of the total area | Rust developed on the total surface |

The surface treating agents of this invention, as demonstrated by the above working examples, show affinity with polyperfluoroalkylene ether oil, barrier characteristic to corrosive materials, and repellency to oil.

Accordingly, the surface treating agents of this invention can be immediately applied onto the surface of a substrate like metal as anti-corrosion and anti-fouling film. The can also be applied either along or in addition to polyperfluoroalkylene ether oil to the systems where polyperfluoroalkylene ether oil has been hitherto used.

The present invention provides surface treating agents useful per se as chemically stable and inert oil, or as oil additives having superior surface activity and anti-corrosive property for metal surface. Thus, these agents have substantial industrial value.

We claim:

1. A titanium fluoropolyether surface active agent selected from a monomeric form having the general formula $$A_aTiB_{(4-a)}$$

where A is a fluoropolyether carboxy group, B is a hydrolyzable radical wherein neither HCl or HBr is generated by hydrolysis, and a is an integer from 1 to 3; and a polymeric form having the formula $$A_aTiO(TiO)_bTiB_{(4-a)}$$

wherein A, B and a have the meanings given above and b is an integer from 0 to 4.

2. Fluoropolyether surface treating agents according to claim 1, in which the hydrolyzable group B is an RO— group in which R is alkyl of 1 to 8 carbon atoms, alkenyl, or an enolate form of β-di-keto-compound or of β-keto-ester.

3. Fluoropolyether surface treating agents according to claim 2, in which B is an enolate form of β-di-keto compound or β-keto-ester selected from the following groups:

wherein Y is a methyl group or an alkoxy group of 1 to 4 carbon atoms.

4. Fluoropolyether surface treating agents according to claim 1 in which B is of the type —NR₁R₂ in which R₁ and R₂ have the same meaning of R as already defined.

5. Fluoropolyether surface treating agents according to claim 1 in which A is a fluoropolyether having a carboxy group and having the following general repeating unit:

$$(C_nF_{2n}O)$$

wherein n ranges from 1 to 3.

6. Fluoropolyether surface treating agents according to claim 1, in which the fluoropolyether of group A has at least one of the following repeating units:

(I) $(CF_2CF_2O)$, and $(CF_2O)$, each of said units being randomly distributed along the perfluoropolyether chain;

(II)

with X=F or CF₃, each of said units being randomly distributed along the perfluoropolyether chain;

(III)

(IV) $(CH_2CF_2CF_2O)$;
(V) $(CF_2CF_2CF_2O)$;
(VI) $-(-CF_2-CF_2-CH_2O)_p-R'_f-O-(CH_2CF_2-CF_2-O)_q-$ wherein R'_f is a fluoroalkylene group, p and q are integers of from 0 to 200, and p+q is at least 2;

(VII)

wherein R''_f is a fluoroalkylene group, n' is either 0 or 1, a and b are integers, and a+b is at least 2;

(VIII) $(CF_2CF_2O)$, (IX)

wherein R_f can be the same or different and are F or a perfluoroalkyl group;

(X) $(CF_2OCF_2CF_2O)$.

7. Fluoropolyether surface treating agents according to claim 6, in which the fluoropolyether is selected from the types: (I), (II), (III), having number average molecular weight ranging from 400 to 8000.

8. Fluoropolyether surface treating agents according to claim 6, in which the carboxy group can be linked to the repeating units through a divalent radical Z:

$$-C_{p''}F_{2p''}-O-(Z)_{p'}-COO-$$

in which p'' is 1 or 2, and p' is 0 or 1 and Z is selected from the following groups:
—(CH$_2$—)$_t$ wherein t=1–4, —CH$_2$OCH$_2$—
—(CH$_2$CH$_2$O)$_t$CH$_2$—, —CONHCH$_2$CH$_2$—.

9. Fluoropolyether surface treating agents according to claim 2, in which R of the RO— group has from 1 to 8 carbon atoms.

10. A surface treating agent composition comprising agent according to claim 1 and a perfluoropolyether oil.

* * * * *

UNITED STATES PATENT AND TRADEMARK OFFICE
CERTIFICATE OF CORRECTION

PATENT NO. : 4,978,389

DATED : December 18, 1990

INVENTOR(S) : MASSAYUCHI SATO et al.

It is certified that error appears in the above-identified patent and that said Letters Patent is hereby corrected as shown below:

Column 1, line 30: Add a comma after "perfluoropolyethers".

Column 1, line 57: Change "to" to --of--.

Column 3, line 23: Change "-(CF$_2$-CF$_2$-CH$_2$O)$_o$-" to -- -(-CF$_2$-CF$_2$-CH$_2$O)$_p$- --.

Column 3, line 64: Change the comma after "87/00538" to a semi-colon.

Column 4, line 30: Change the equal signs to dashes.

Column 6, lines 40-41: Delete "BEST MODE FOR CARRYING OUT THE INVENTION"

Column 7, line 45: Change "acetone" to --acetylacetone--.

In claim 6 part (I)

Column 10, line 27: Add --and-- before "(CFXO)".

UNITED STATES PATENT AND TRADEMARK OFFICE
CERTIFICATE OF CORRECTION

PATENT NO. : 4,978,389

DATED : December 18, 1990

INVENTOR(S) : Massayuchi Sato, et al.

It is certified that error appears in the above-identified patent and that said Letters Patent is hereby corrected as shown below:

Column 10, line 27, add --and-- before "(CFXO)".

Signed and Sealed this

Twenty-ninth Day of September, 1992

Attest:

DOUGLAS B. COMER

*Attesting Officer*  Acting Commissioner of Patents and Trademarks